US005195139A

United States Patent [19]

Gauthier

[11] Patent Number: 5,195,139

[45] Date of Patent: Mar. 16, 1993

[54] HEARING AID

[75] Inventor: Edouard A. Gauthier, West Chester, Pa.

[73] Assignee: Ensoniq Corporation, Malvern, Pa.

[21] Appl. No.: 700,581

[22] Filed: May 15, 1991

[51] Int. Cl.[5] ..................... H04R 25/00; H04R 25/02; A61B 7/02

[52] U.S. Cl. ........................................ 381/69; 381/68; 381/68.6; 181/130; 181/135

[58] Field of Search ....................... 381/69, 68.6, 68.7, 381/69.1, 69.2, 93, 83; 181/135, 130, 129, 160

[56] References Cited

U.S. PATENT DOCUMENTS 4,311,206 1/1982 Johnson ............................ 381/68.6
4,712,245 12/1987 Lyregaard .
4,852,177 7/1989 Ambrose ............................ 181/135
5,033,090 7/1991 Weinrich ........................... 381/68.6

FOREIGN PATENT DOCUMENTS 0445203 11/1991 European Pat. Off. .
3927797 2/1991 Fed. Rep. of Germany .

*Primary Examiner*—James L. Dwyer
*Assistant Examiner*—Fan Tsang
*Attorney, Agent, or Firm*—Ratner & Prestia

[57] ABSTRACT

A hearing aid in which selected frequency components of sound being vented from the ear canal of the user of the hearing aid to eliminate the "occlusion effect" are conducted to an acoustically isolated cavity to eliminate, or greatly reduce, feedback in the hearing aid.

7 Claims, 1 Drawing Sheet

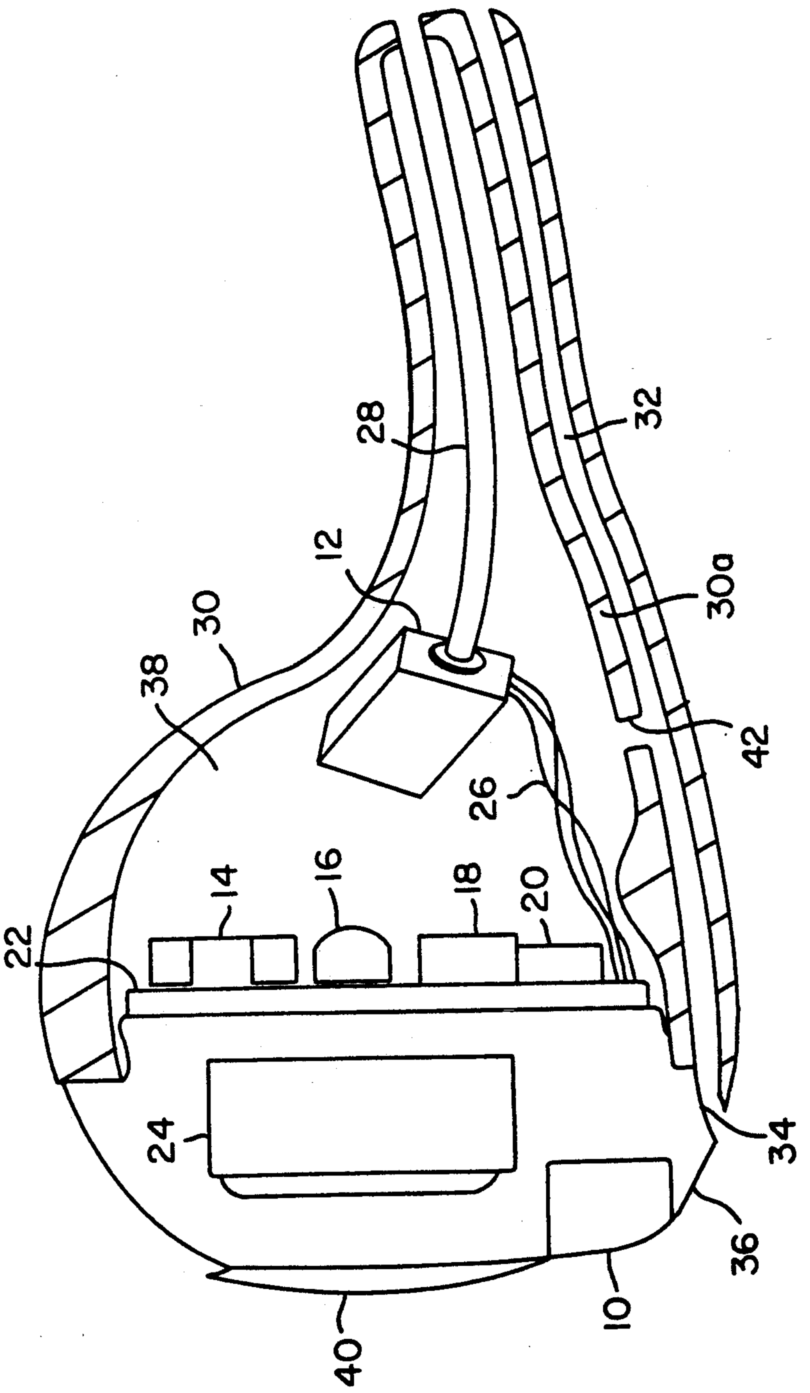
28
32
12
30
38
30a
42
26
14
16
18
20
22
24
34
36
10
40

HEARING AID

TECHNICAL FIELD

The present invention relates, in general, to hearing aids and, in particular, to a hearing aid in which feedback from the hearing aid speaker to the hearing aid microphone is greatly reduced.

BACKGROUND OF THE INVENTION

When a hearing aid ear mold housing is placed in the ear, a phenomenon known as "occlusion effect" occurs. The voice of the hearing aid user is conducted through his skull to his ear canal. The "occlusion effect" causes the voice of the hearing aid user to sound very loud.

The "occlusion effect" is greatly reduced, if not eliminated entirely, in many commercially available hearing aids by providing a small air vent passage, typically in an outside wall of the ear mold housing of the hearing aid, through which sounds in the ear canal of the ear, produced by the "occlusion effect," are "vented" to outside the ear. Because the "occlusion effect" is most evident at low frequencies, the air vent passage is designed for passage of the low frequency components of the voice of the hearing aid user.

Unfortunately, the small air vent passage also allows a portion of the amplified sound produced by the hearing aid speaker to escape. If this escaping sound is loud enough, feedback will occur. The frequency range of the feedback, typically between 2.0 kHz and 6.5 kHz, is dependent upon the spacing of the hearing aid microphone and hearing aid speaker, the length of the air vent passage, and the gain of the hearing aid.

SUMMARY OF THE INVENTION

A hearing aid, constructed in accordance with the present invention, includes transmitter means, including a microphone, responsive to external sounds for developing electrical signals representative of the external sounds and receiver means, including a speaker, responsive to the electrical signals for producing amplified versions of the external sounds. For a hearing aid which is completely contained within the ear of the hearing aid user, the transmitter means and receiver means are contained in a housing molded to fit the ear of the hearing aid user. This hearing aid also includes a cavity which is acoustically isolated from outside the ear of the user of the hearing aid and the ear canal of the user of the hearing aid. Also included in this hearing aid are means for conducting sounds from the ear canal of the user of the hearing aid to outside the ear. Such means are provided to eliminate the "occlusion effect." Further, this hearing aid includes means, extending between the acoustically isolated cavity and the means by which sounds from the ear canal are conducted to outside the ear, for conducting selected frequency components of this sound into the acoustically isolated cavity. Such means are provided to eliminate, or greatly reduce, feedback in the hearing aid.

BRIEF DESCRIPTION OF THE DRAWING

The single FIGURE is a sectional view of one preferred embodiment of a hearing aid constructed in accordance with the present invention.

DETAILED DESCRIPTION OF THE INVENTION

Referring to the drawing, a hearing aid, constructed in accordance with the present invention, includes transmitter means and receiver means which can be of conventional construction and operation and are represented in the drawing by a microphone 10, a speaker 12, the various electrical components 14, 16, 18 and 20 mounted on a printed circuit board 22, a battery housed in a battery compartment 24, and wires 26 running from printed circuit board 22 to speaker 12. Speaker 12 has a sound conducting tube 28 which opens to the ear canal of the user of the hearing aid when the hearing aid is positioned in the ear. For a hearing aid which is completely contained within the ear of the hearing aid user, the transmitter means and receiver means are contained in a housing molded to fit the ear of the hearing aid user.

Microphone 10 responds to external sounds and the transmitter means develop electrical signals representative of the external sounds. The receiver means respond to the electrical signals and speaker 12 produces amplified versions of the external sounds which are conducted to the ear canal of the hearing aid user by sound conducting tube 28.

A hearing aid, constructed in accordance with the present invention, also includes a housing 30. Housing 30 has an air vent passage 32 extending along the length of the housing. Preferably, air vent passage 32 extends through an outside wall 30*a* of the housing. Air vent passage 32 conducts sound from the ear canal of the hearing aid user to outside the ear and is provided to eliminate the "occlusion effect" as described above. For the embodiment of the present invention illustrated in the drawing, an extension of air vent passage 32 is provided by a short passage 34 in a plate 36.

Plate 36 extends across housing 30 and forms a cavity 38 within the housing which is acoustically isolated from outside the ear of the hearing aid user and the ear canal of the hearing aid user. The acoustic isolation is achieved by a suitable adhesive applied at the contact surfaces of the mating parts to form an acoustic seal. For the embodiment of the present invention illustrated in the drawing, speaker 12 is positioned within cavity 38. Amplified versions of external sounds, produced by the usual cooperation of the transmitter means and the receiver means, are conducted to the ear canal of the hearing aid user.

Plate 36 is arranged to contain microphone 10 and battery compartment 24. A battery compartment door 40 is provided to gain access to battery compartment 24 to change the battery.

Housing 30 also has a tuned passage 42 extending through wall 30*a* of the housing from air vent passage 32 to cavity 38. Tuned passage 42 and cavity 38 form a Helmholtz resonator which resonates at a frequency determined by the following, well known equation:

$$\omega_o = c \times \sqrt{A/l \times V}$$

where:

c is the speed of sound in meters/second
A is the cross-sectional area of tuned passage 42
l is the length of tuned passage 42
V is the volume of cavity 38

Thus, for a given hearing aid having an air vent passage, the size of tuned passage 42 (i.e. its length and cross-sectional area) are selected to "trap" those frequency components which would otherwise cause feedback in the absence of tuned passage 42.

Although the present invention has been described in connection with a hearing aid which is completely contained within the ear of the hearing aid user, it will be apparent that, with suitable modifications and substitutions, the present invention also has application in "behind the ear" hearing aids, although the feedback problem is less severe in such instruments because of the greater spacing between the hearing aid microphone and the hearing aid speaker.

While a preferred embodiment of the present invention has been described and certain modifications and substitutions are suggested, it will be apparent to those skilled in the art that various other modifications and substitutions can be made without departing from the true spirit and scope of the invention. Accordingly, it is understood that the present invention has been described by way of illustration and not limitation.

What is claimed:

1. A hearing aid comprising:
transmitter means, including a microphone, responsive to external sounds for developing electrical signals representative of said external sounds;
receiver means, including a speaker, responsive to said electrical signals for producing amplified versions of said external sounds;
and a housing having:
(a) an air vent passage extending along the length of said housing for conducting sound from the ear canal of a user of said hearing aid to outside the ear,
(b) an isolation wall extending across said housing forming within said housing a cavity acoustically isolated from outside the ear of the user of said hearing aid and the ear canal of the user of said hearing aid, and
(c) a tuned passage extending from said air vent passage and opening into said cavity.

2. A hearing aid according to claim 1 wherein said air vent passage is in an outside wall of said housing and said tuned passage extends through said outside wall from said air vent passage to said cavity.

3. A hearing aid according to claim 2 wherein said speaker is positioned within said cavity.

4. A hearing aid comprising:
transmitter means, including a microphone, responsive to external sounds for developing electrical signals representative of said external sounds;
receiver means, including a speaker, responsive to said electrical signals for producing amplified versions of said external sounds;
a cavity acoustically isolated from outside the ear of the user of said hearing aid and the ear canal of the user of said hearing aid;
means for conducting sounds from the ear canal of an ear with which said hearing aid is used to outside the ear;
and means extending between said cavity and said sound conducting means for conducting selected frequency components of said sound from said sound conducting means into said cavity.

5. A hearing aid comprising:
transmitter means, including a microphone, responsive to external sounds for developing electrical signals representative of said external sounds;
receiver means, including a speaker, responsive to said electrical signals for producing amplified versions of said external sounds;
means for conducting sounds from the ear canal of the user of said hearing aid to outside the ear of the user of said hearing aid;
and a Helmholtz resonator acoustically coupled to said sound conducting means for filtering frequency components between 2.0 kHz and 6.5 kHz from the sounds conducted from the ear canal of the user of said hearing aid to outside the ear of the user of said hearing aid.

6. A hearing aid according to claim 5 wherein said Helmholtz resonator includes:
(a) a cavity acoustically isolated from outside the ear of the user of said hearing aid and the ear canal of the user of said hearing aid, and
(b) a passage extending between said cavity and said sound conducting means.

7. A hearing aid comprising:
transmitter means, including a microphone, responsive to external sounds for developing electrical signals representative of said external sounds;
receiver means, including a speaker, responsive to said electrical signals for producing amplified versions of said external sounds;
means for conducting sounds from the ear canal of the user of said hearing aid to outside the ear of the user of said hearing aid;
a cavity acoustically isolated from outside the ear of the user of said hearing aid and the ear canal of the user of said hearing aid;
and a tuned passage extending from said sound conducting means and opening into said cavity.

* * * * *